US008068133B2

(12) United States Patent
Arai et al.

(10) Patent No.: US 8,068,133 B2
(45) Date of Patent: Nov. 29, 2011

(54) IMAGE PROCESSING APPARATUS AND IMAGE PROCESSING METHOD

(75) Inventors: Satoshi Arai, Hachioji (JP); Tokiya Abe, Boston, MA (US); Masahiro Yamaguchi, Yokohama (JP)

(73) Assignee: Olympus Corporation, Tokyo (JP)

( * ) Notice: Subject to any disclaimer, the term of this patent is extended or adjusted under 35 U.S.C. 154(b) by 501 days.

(21) Appl. No.: 12/380,137

(22) Filed: Feb. 24, 2009

(65) Prior Publication Data

US 2009/0231421 A1   Sep. 17, 2009

Related U.S. Application Data

(63) Continuation of application No. PCT/JP2007/065979, filed on Aug. 10, 2007.

(30) Foreign Application Priority Data

Aug. 24, 2006 (JP) ................................. 2006-228269

(51) Int. Cl.
 *H04N 7/18* (2006.01)
(52) U.S. Cl. ....... 348/79; 348/223.1; 382/128; 382/132; 382/275; 382/167; 378/5; 378/86; 378/98.9; 378/98.11; 378/98.12
(58) Field of Classification Search .................... 348/79, 348/223.1
See application file for complete search history.

(56) References Cited

U.S. PATENT DOCUMENTS

| | | | |
|---|---|---|---|
| 6,549,653 B1 * | 4/2003 | Osawa et al. | ................ 382/162 |
| 7,010,162 B2 * | 3/2006 | Osawa et al. | ................ 382/167 |

FOREIGN PATENT DOCUMENTS

| | | |
|---|---|---|
| JP | 2002-149148 | 5/2002 |
| JP | 2003-065948 | 3/2003 |
| JP | 2005-315877 | 11/2005 |

OTHER PUBLICATIONS

Abe, Tokiya et al., "Color Correction of Pathological Images Based on Dye Amount Quantification", Optical Review (2005), pp. 293-300, vol. 12, No. 4, The Optical Society of Japan.
Abe, Tokinari et al., "Multi Spectrum Gazo o Mochiita Byori Gazo no Shikisoryo no Teiryoka to Iro Hyojunka-Band-su to Keisan Seido no Kento", Medical Imaging Technology (Jan. 25, 2006), pp. 38-47, vol. 24, No. 1.

* cited by examiner

*Primary Examiner* — Jude Jean Gilles
(74) *Attorney, Agent, or Firm* — Scully, Scott, Murphy & Presser, P.C.

(57) ABSTRACT

An image processing apparatus includes a first spectrum estimating unit for reading the image information from a storage unit and estimating a spectrum of an object based on the read image information; a dye amount estimating unit for estimating dye amounts included in the object using the estimated spectrum; a second spectrum estimating unit for synthesizing a first spectrum using the estimated dye amounts; a spectrum subtractor for calculating a difference spectrum by subtracting the first spectrum from the spectrum; a dye amount correcting unit for correcting at least a part of the estimated dye amounts; a third spectrum estimating unit for synthesizing a second spectrum using the corrected dye amount; a spectrum adder for synthesizing a third spectrum by adding the second spectrum and the difference spectrum; and an image synthesizer for synthesizing a display image from the third spectrum.

22 Claims, 9 Drawing Sheets
(2 of 9 Drawing Sheet(s) Filed in Color)

IMAGE PROCESSING APPARATUS AND IMAGE PROCESSING METHOD

CROSS-REFERENCE TO RELATED APPLICATIONS

This application is a continuation of PCT international application Ser. No. PCT/JP2007/065979 filed on Aug. 10, 2007 which designates the United States, incorporated herein by reference, and which claims the benefit of priority from Japanese Patent Application No. 2006-228269, filed on Aug. 24, 2006, incorporated herein by reference.

BACKGROUND OF THE INVENTION

1. Field of the Invention

The present invention relates to an image processing technology of a dye-stained living specimen, and specifically relates to an image processing apparatus, an image processing method, and an image processing program for forming a display image from image data obtained by imaging a pathological specimen with multiband using transmitting illumination.

2. Description of the Related Art

In the living specimen, especially in the pathological specimen, magnifying observation with a microscope for acquiring various findings is widely performed after thinly slicing a block specimen obtained by removing an organ and the specimen obtained by performing a needle biopsy to approximately several micrometers. Among them, transmitting observation with an optical microscope is one of the most popular observation methods, because equipments are relatively inexpensive and easy to handle, and this has been performed through the ages. In this case, the thinly sliced living specimen hardly absorbs or scatters light and is nearly clear and colorless, so that this is generally stained by dye before the observation.

Conventionally, various types of staining methods have been suggested, and a total number thereof rises to 100 or larger; however, regarding especially the pathological specimen, hematoxylin-eosin staining (hereinafter, referred to as "H&E staining") using blue-purple hematoxylin and red eosin as dyes is normally used.

Hematoxylin is a natural substance collected from a plant, and has no staining properties in itself. However, hematin, which is oxide thereof, is a basophilic dye, and combines with a negatively charged substance. Deoxyribo nucleic acid (DNA) in a cell nucleus is negatively charged by a phosphate group contained as a component, so that this combines with hematin and is stained in blue-purple. Meanwhile, as described above, although hematin, which is the oxide of hematoxylin, has the staining properties, this is hereinafter referred to as hematoxylin because this is general as the name of dye.

Eosin is an acidophilic dye and combines with a positively charged substance. A pH environment affects the charge of amino acid and protein, and they tend to be positively charged under an acidic condition. Therefore, eosin solution is sometimes used with acetic acid added thereto. The protein in a cytoplasm combines with eosin and is stained to red to pink.

In the specimen after the H&E staining, the cell nucleus, bone tissue, and the like are stained in blue-purple, and the cytoplasm, connective tissue, and a red blood cell are stained in red, respectively, and are easily visually recognized. As a result, an observer may comprehend sizes of components composing the tissue such as the cell nucleus and a positional relationship among them, so that it becomes possible to morphologically judge a state of the specimen.

The staining of the living specimen is an operation to fix the dye to living tissue originally having individual difference using chemical reaction, so that it is difficult to obtain an always uniform result. Specifically, even when the specimen is allowed to react with staining solution of the same concentration for the same time period, an amount of the dye to be fixed is not always nearly equal. According to the specimens, there are cases in which relatively more dyes are fixed and in which relatively less dyes are fixed. In the former case, the specimen is stained deeper than the general one; on the other hand, in the latter case, the specimen is stained lighter than the general one. There are facilities staffed with a stain engineer having specialized skills in order to prevent such variation in staining. In such facilities, the staining variation in the same facilities may be reduced to a certain degree by a professional adjustment operation by the stain engineer, but it is not possible to reduce the staining variation of other facilities.

The above-described staining variation has two problems. First, when a human visually observes, irregularity in states of the observation objects might cause stress of the observer. Especially, when there is significant variation, possibility of overlooking crucial finding cannot be denied.

Second, when imaging the stained specimen with a camera and image-processing the same, the staining variation might badly affect process accuracy. For example, even when it is known that a certain lesion displays a specific color, it is difficult to automatically extract this fact from the image. This is because the staining variation disturbs the color variation due to the lesion.

A method for solving such a problem in the staining variation by the image processing using a multiband image is disclosed in Tokiya Abe et al., "Color Correction of Pathological Images Based on Dye Amount Quantification", OPTICAL REVIEW Vol. 12, No. 4 (2005) 293-300 (hereinafter, referred to as a non-patent document). In the non-patent document, a relative amount of the dye (dye amount) fixed from the multiband image to the stained specimen is estimated based on a predetermined physical model. Next, the estimated dye amount is virtually increased or decreased, and further a color image of the virtual specimen is synthesized using the increased or decreased dye amount. By appropriately increasing and decreasing the dye amount, the deeply stained specimen and the lightly stained specimen can be corrected to the image having the color nearly equal to the appropriately stained specimen. Hereinafter, the correction technique of the image disclosed in the above-described non-patent document will be described in more detail.

First, the multiband image is imaged with a frame sequential method by rotating 16 band path filters with a filter wheel to switch. Such an imaging method is disclosed in, for example, Japanese Patent Application Laid-Open No. 07-120324. With this imaging method, the multiband image having a 16-band pixel value at each point of the specimen is obtained.

The dyes are originally three-dimensionally distributed in the stained specimen, which is the observation object, but it is not possible to directly acquire the same as a three-dimensional image by a general transmitting observation system, and this is observed as a two-dimensional image obtained by projecting illuminating light passing through the specimen on an imaging device of the camera. Therefore, the above-described each point of the specimen means the point on the projected specimen corresponding to each pixel of the imaging device.

A relationship represented by the following equation (1) is established among a position (x, y) of the image, a pixel value g(x, y, b) in a band b, and a spectral transmittance t(x, y, λ) of a corresponding point on the specimen.

$$g(x,y,b) = \int f(b, \lambda) s(\lambda) e(\lambda) t(x,y,\lambda) d\lambda + n(b) \quad (1)$$

where $\lambda$ represents a wavelength, $f(b, \lambda)$ represents a spectral transmittance of a b-th filter, $s(\lambda)$ represents spectral sensitivity characteristics of the camera, $e(\lambda)$ represents spectral radiance characteristics of the illumination, and $n(b)$ represents imaging noise in the band b. Meanwhile, b is a sequential number for identifying the band, and is an integral value satisfying $1 \leq b \leq 16$.

In an actual calculation, the following equation (2), which is obtained by discretizing the equation (1) in a wavelength direction, is used.

$$G(x,y) = FSET(x,y) + N \quad (2)$$

Here, when a sampling number in the wavelength direction and the number of bands are set to D and B (wherein B=16), respectively, G(x, y) is a B-row 1-column matrix corresponding to the pixel value g(x, y, b) at the position (x, y). Similarly, T(x, y) is a D-row 1-column matrix corresponding to t(x, y, λ), and F is a B-row D-column matrix corresponding to f(b, λ). S is a D-row D-column diagonal matrix and a diagonal component corresponds to s(λ). E also is a D-row D-column diagonal matrix and the diagonal component corresponds to e(λ). N is a B-row 1-column matrix corresponding to n(b). In the equation (2), since the equations regarding a plurality of bands are summarized using the matrix, a variable b representing a band is not explicitly expressed. Also, integration of the wavelength λ is substituted by a matrix product.

Next, the spectral transmittance at each point of the specimen is estimated from the imaged multiband image. Wiener estimation is used as the estimation method at that time.

The Wiener estimation is widely known as one of linear filter methods for estimating an original signal from a signal on which noise is superimposed, and an estimation value $\hat{T}(x,y)$ of the spectral transmittance can be calculated by the following equation (3).

$$\hat{T}(x,y) = R_{SS}(FSE)^t((FSE)R_{SS}(FSE)^t + R_{NN})^{-1}G(x,y) \quad (3)$$

where $R_{SS}$ is a D-row D-column matrix and represents an autocorrelation matrix of the spectral transmittance of the specimen of the object specimen. $R_{NN}$ is a B-row B-column matrix and represents the autocorrelation matrix of noise of the camera used for imaging. Also, $(\ )^t$ and $(\ )^{-1}$ represent a transposed matrix and an inverse matrix, respectively. Hereinafter, $\hat{T}$ is sometimes represented as $T\hat{\ }$ (this notation applies to a case of a letter other than T).

Next, the dye amounts at each point (x, y) of the specimen are estimated based on the estimated spectral transmittance $T\hat{\ }(x, y)$. Here, the dyes, which are objects of the estimation, are hematoxylin, eosin which stains the cytoplasm, and eosin which stains the red blood cell. Hereinafter, for simplicity, the above-described three kinds of dyes are abbreviated as a dye H, a dye E, and a dye R in this order. Meanwhile, to be strict, the red blood cell has its particular color even in a state without staining, and after the H&E staining, the color of the red blood cell itself and the color of eosin changed in the course of staining are superimposingly observed. Therefore, to be precise, the color obtained by superimposing the color of the red blood cell itself on the color of eosin, which stains the red blood cell, is referred to as the dye R.

Generally, it is known that in a light transmissive substance, a Lambert-Beer law represented by the following equation (4) is established between intensity $I_0(\lambda)$ of incident light and intensity $I(\lambda)$ of emitting light for each wavelength $\lambda$.

$$\frac{I(\lambda)}{I_0(\lambda)} = \exp(-k(\lambda) \cdot d) \quad (4)$$

where $k(\lambda)$ and d represent a substance-specific value decided depending on the wavelength $\lambda$ and thickness of the substance, respectively. Also, the left side of the equation (4) represents the spectral transmittance.

When the H&E stained specimen is stained by three kinds of dyes H, E and R, the following equation (5) is established in each wavelength $\lambda$ by the Lambert-Beer law.

$$\frac{I(\lambda)}{I_0(\lambda)} = \exp(-(k_H(\lambda) \cdot d_H + k_E(\lambda) \cdot d_E + k_R(\lambda) \cdot d_R)) \quad (5)$$

where $k_H(\lambda)$, $k_E(\lambda)$ and $k_R(\lambda)$ represent $k(\lambda)$ corresponding to the dyes H, E and R, respectively. Also, $d_H$, $d_E$ and $d_R$ represent virtual thicknesses corresponding to the dyes H, E and R, respectively. Originally, the dyes are dispersively present in the specimen, so that a concept of width is not correct; however, this becomes an index to indicate a relative dye amount indicating the relative amount of the dye which is present compared to a case supposing that the specimen is stained by a single dye. That is to say, it can be said that $d_H$, $d_E$ and $d_R$ represent the dye amounts of the dyes H, E and R, respectively. $k_H(\lambda)$, $k_E(\lambda)$ and $k_R(\lambda)$ can be easily obtained from the equation (4) by creating the specimen stained by a single dye in advance and measuring the spectral transmittance thereof by a spectrometer.

The following equation (6) is obtained by taking a natural logarithm of both sides of the equation (5).

$$-\log \frac{I(\lambda)}{I_0(\lambda)} = k_H(\lambda) \cdot d_H + k_E(\lambda) \cdot d_E + k_R(\lambda) \cdot d_R \quad (6)$$

The component corresponding to the wavelength $\lambda$ of the estimation value $T\hat{\ }(x, y)$ of the spectral transmittance at the position (x, y) on the specimen obtained by using the equation (3) is represented as $t\hat{\ }(x, y, \lambda)$, and by substituting this $t\hat{\ }(x, y, \lambda)$ into the equation (6), the following equation (7) is obtained.

$$-\log \hat{t}(x,y,\lambda) = k_H(\lambda) \cdot d_H + k_E(\lambda) \cdot d_E + k_R(\lambda) \cdot d_R \quad (7)$$

In this equation (7), unknown variables are three, which are $d_H$, $d_E$ and $d_R$, so that it is possible to make the equation (7) simultaneous with at least three different wavelengths $\lambda$ to solve. In order to further improve accuracy, it is possible to make the equation (7) simultaneous with four or more different wavelengths $\lambda$ to perform a multiple regression analysis.

Once the dye amounts $d_H$, $d_E$ and $d_R$ are obtained, it is possible to simulate the variation in the dye amounts in the specimen by correcting them. That is to say, by multiplying appropriate coefficients $\alpha_H$, $\alpha_E$ and $\alpha_R$, by $d_H$, $d_E$ and $d_R$, respectively, and substituting them into the equation (5), an equation (8) is obtained as a new spectral transmittance $t^*(x, y, \lambda)$.

$$t^*(x,y,\lambda) = \exp(-(k_H(\lambda) \cdot \alpha_H d_H + k_E(\lambda) \cdot \alpha_E d_E + k_R(\lambda) \cdot \alpha_R d_R)) \quad (8)$$

By substituting the equation (8) into the equation (1), the image of the specimen of which dye amount is virtually changed may be synthesized. In this case, however, it is possible to calculate by setting the noise n(b) to 0.

By the above-described procedure, it becomes possible to virtually adjust the dye amounts of the stained specimen. By preparing an appropriate user interface, a user himself may adjust the dye amount and confirm the result by the image. Therefore, even when there is staining variation in the stained specimen, the user may adjust the same to an appropriate staining state to observe, and the problem in the staining variation may be solved.

SUMMARY OF THE INVENTION

An image processing apparatus according to an aspect of the present invention performs an image processing on an image. The image processing apparatus includes a storage unit for storing image information regarding the image; a first spectrum estimating unit for reading the image information from the storage unit and estimating a spectrum of an object based on the read image information; a dye amount estimating unit for estimating a plurality of dye amounts included in the object using the spectrum of the object estimated by the first spectrum estimating unit; a second spectrum estimating unit for synthesizing a first spectrum using the plurality of dye amounts estimated by the dye amount estimating unit; a spectrum subtractor for calculating a difference spectrum by subtracting the first spectrum synthesized by the second spectrum estimating unit from the spectrum of the object; a dye amount correcting unit for correcting at least a part of the plurality of dye amounts estimated by the dye amount estimating unit; a third spectrum estimating unit for synthesizing a second spectrum using the dye amount corrected by the dye amount correcting unit; a spectrum adder for synthesizing a third spectrum by adding the second spectrum synthesized by the third spectrum estimating unit and the difference spectrum; and an image synthesizer for synthesizing a display image from the third spectrum synthesized by the spectrum adder.

An image processing method according to another aspect of the present invention is for performing an image processing on an image. The image processing method includes reading the image information from a storage unit; estimating a spectrum of an object based on the read image information; estimating a plurality of dye amounts included in the object using the estimated spectrum of the object; synthesizing a first spectrum using the estimated dye amounts; calculating a difference spectrum by subtracting the first spectrum from the spectrum of the object; correcting at least a part of the estimated dye amounts; synthesizing a second spectrum using the corrected dye amount; synthesizing a third spectrum by adding the second spectrum; and synthesizing a display image from the third spectrum.

A computer program product according to still another aspect of the present invention causes a computer to perform the method according to the present invention.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Hereinafter, a best mode for carrying out the present invention (hereinafter, referred to as an "embodiment") will be described with reference to the attached drawings.

In one embodiment of the present invention, a 6-band image of an H&E stained pathological specimen is imaged with two kinds of optical filters and an RGB camera, and spectral transmittance characteristics and a dye amount are estimated for each point of an object. Thereafter, the estimated dye amount is corrected and the corrected dye amount is converted again to the spectral transmittance characteristics to be converted to an RGB value. This embodiment is characterized in that only the dye amounts of hematoxylin and eosin in a cytoplasm other than a red blood cell are used when converting from the dye amount to spectral transmittance, and another component is processed as a difference spectrum.

Figure 1:
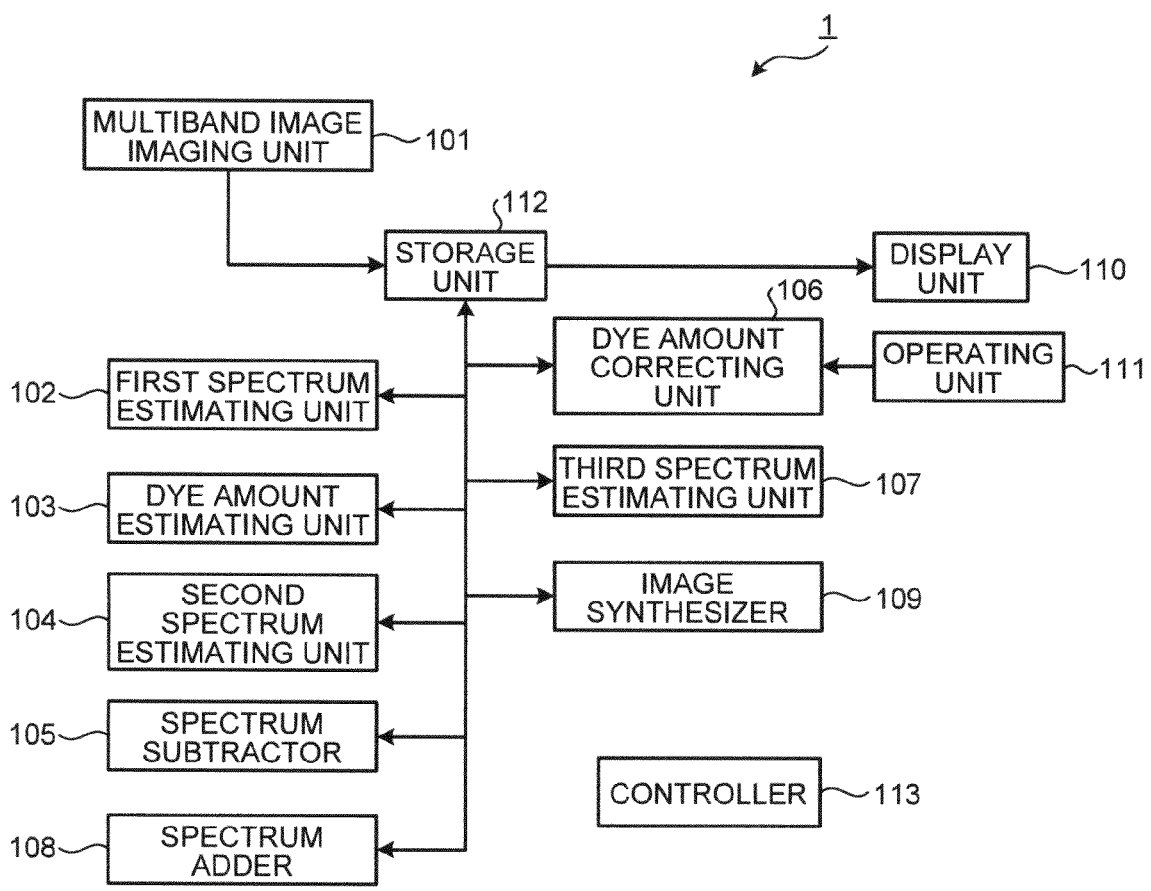
FIG. 1 is a view showing a configuration of an image processing apparatus according to one embodiment of the present invention.

FIG. 1 is a view showing a configuration of an image processing apparatus 1 according to this embodiment. The image processing apparatus 1 shown in the drawing is provided with a multiband image imaging unit 101, a first spectrum estimating unit 102, a dye amount estimating unit 103, a second spectrum estimating unit 104, a spectrum subtractor 105, a dye amount correcting unit 106, a third spectrum estimating unit 107, a spectrum adder 108, an image synthesizer 109, a display unit 110, an operating unit 111, a storage unit 112, and a controller 113 for controlling operations of all of them. Meanwhile, in FIG. 1, connections from the controller 113 to each unit are not shown. The image processing apparatus 1 is composed of a computer provided with a CPU, a ROM, a RAM, and the like.

Figure 2:
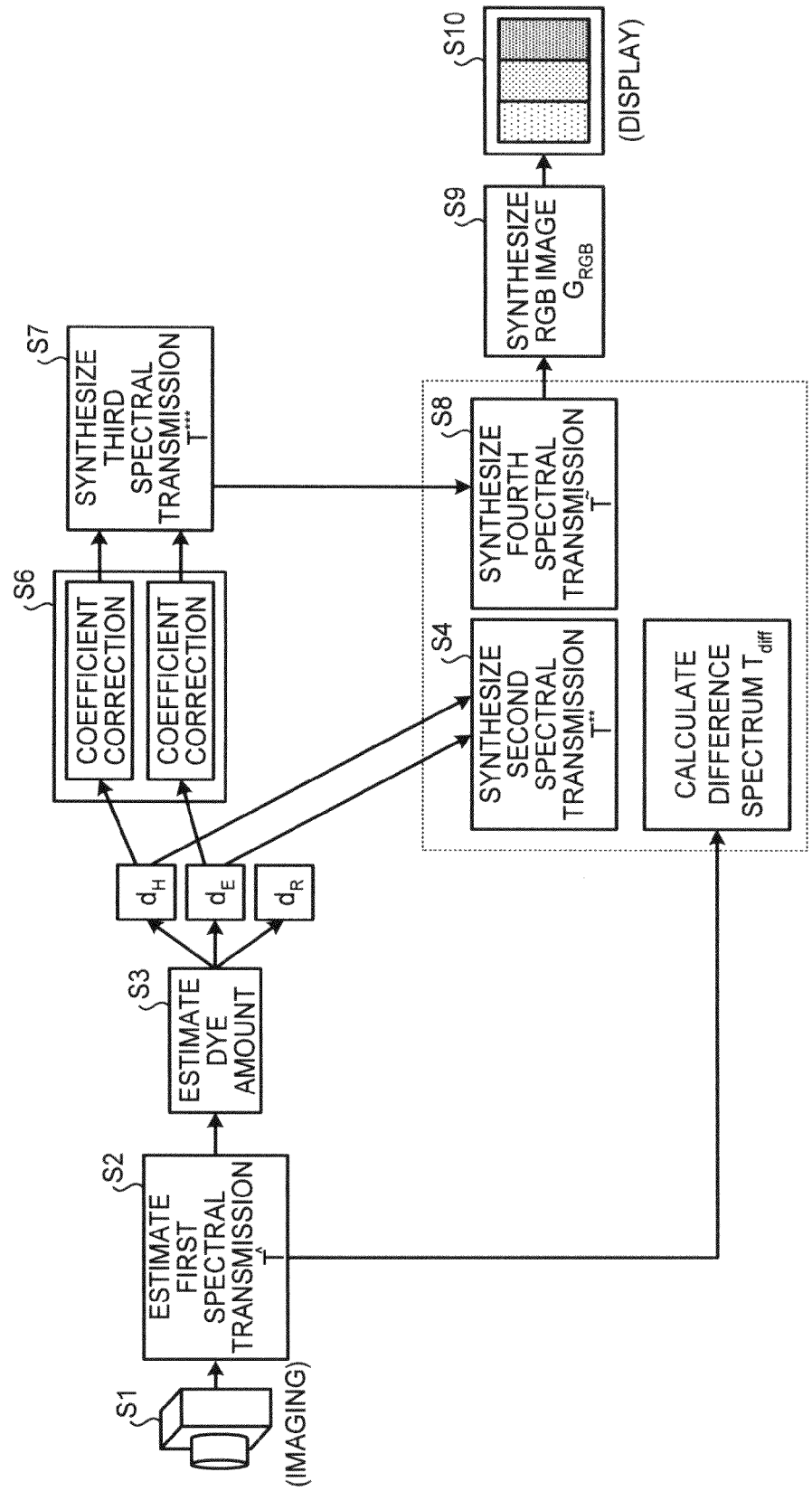
FIG. 2 is a view showing an overview of a process of an image processing method according to one embodiment of the present invention.

FIG. 2 is a view showing an overview of an image processing method according to this embodiment. Hereinafter, a functional configuration of the image processing apparatus 1 and the overview of the image processing method are described with reference to FIGS. 1 and 2, respectively.

Figure 3:
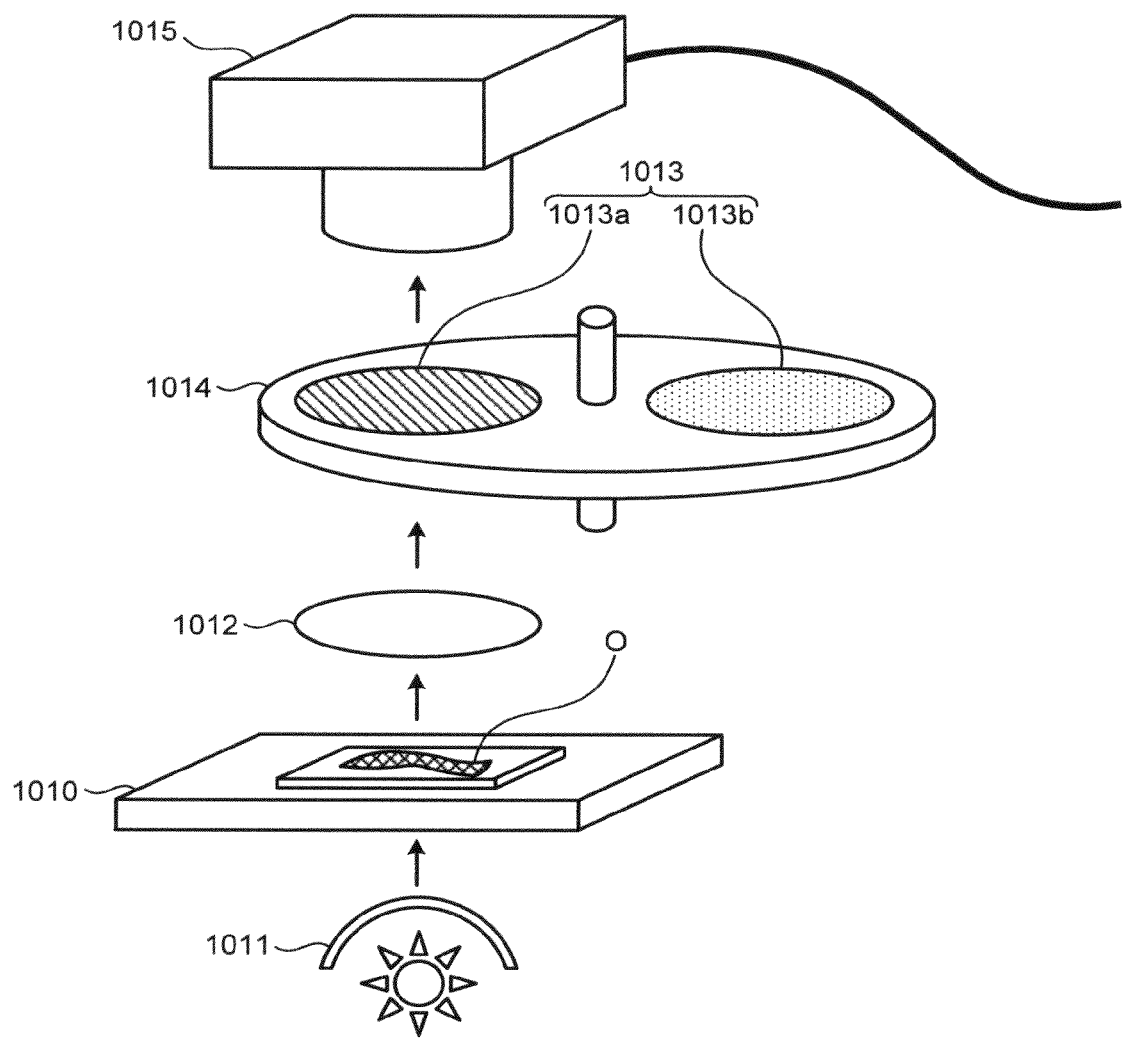
FIG. 3 is a view showing a configuration of a multiband image imaging unit.

First, an object specimen is imaged as a 6-band multiband image by the multiband image imaging unit 101 (step S1). The multiband image imaging unit 101 is composed of a specimen holder 1010, an illuminating unit 1011, an optical system 1012, an optical filter 1013, an optical filter switching unit 1014, and an RGB camera 1015, as shown in FIG. 3.

Figures 4, 5:
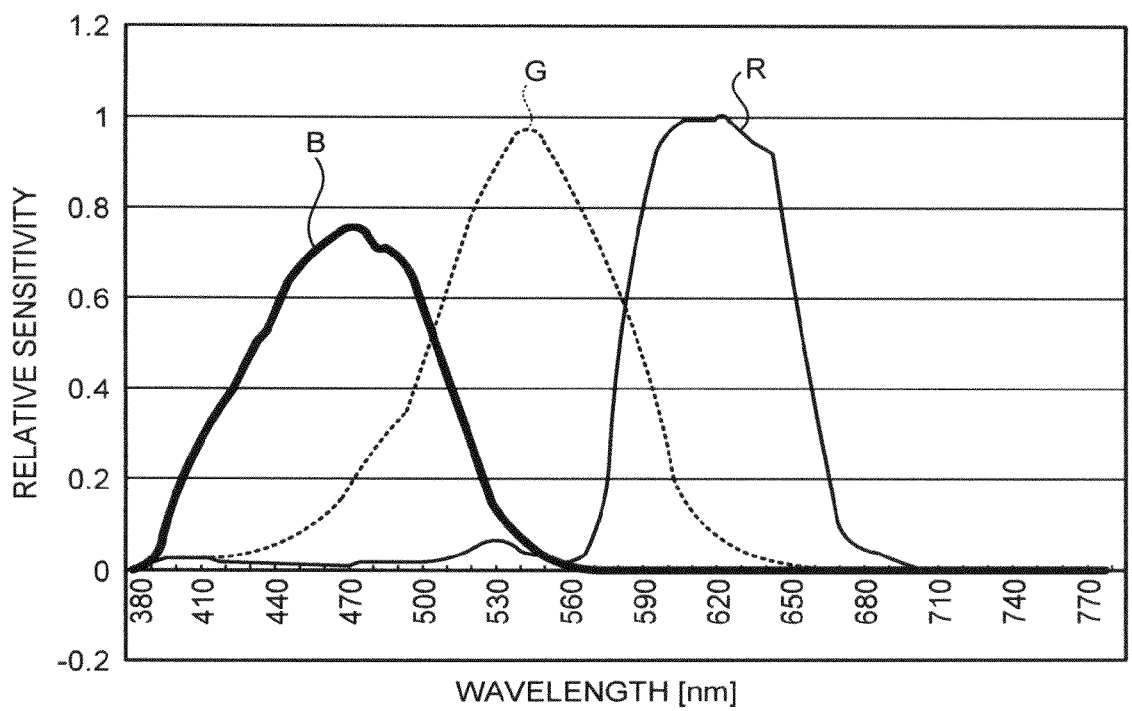
FIG. 4 is a view schematically showing a configuration example of an RGB filter.
FIG. 5 is a view showing an example of spectral sensitivity of each of R, G, B bands.

The RGB camera 1015 used here is one widely used in a digital camera or the like, and is obtained by arranging RGB filters on a black-and-white imaging device in a mosaic pattern. FIG. 4 is a view schematically showing a configuration example of the RGB filter. When using an RGB filter 200 shown in the drawing, although each pixel can only image any one of components R, G and B, a method for interpolating lacking R, G and B components by utilizing pixel values in the vicinity of each of them is adopted. Meanwhile, this method is disclosed in Japanese Patent No. 3510037, for example.

On the other hand, it is also possible to image with a 3CCD-type camera. In this case, the R, G and B components in each pixel can be obtained from the beginning.

Although both of the above-described imaging methods may be used in this embodiment, in a process to be described below, it is assumed that the R, G and B components are obtained in each pixel of the image imaged with the RGB camera 1015.

Light emitted by the illuminating unit 1011 passes through a specimen O placed on the specimen holder 1010. The transmitting light forms an image on the imaging device of the RGB camera 1015 through the optical system 1012 and the optical filter 1013. The optical filter 1013 has only to be placed on any position on an optical path from the illuminating unit 1011 to the RGB camera 1015. FIG. 5 shows an example of spectral sensitivity of each of R, G and B bands when imaging the illuminating light from the illuminating unit 1011 with the RGB camera 1015 through the optical system 1012.

Figure 6A:
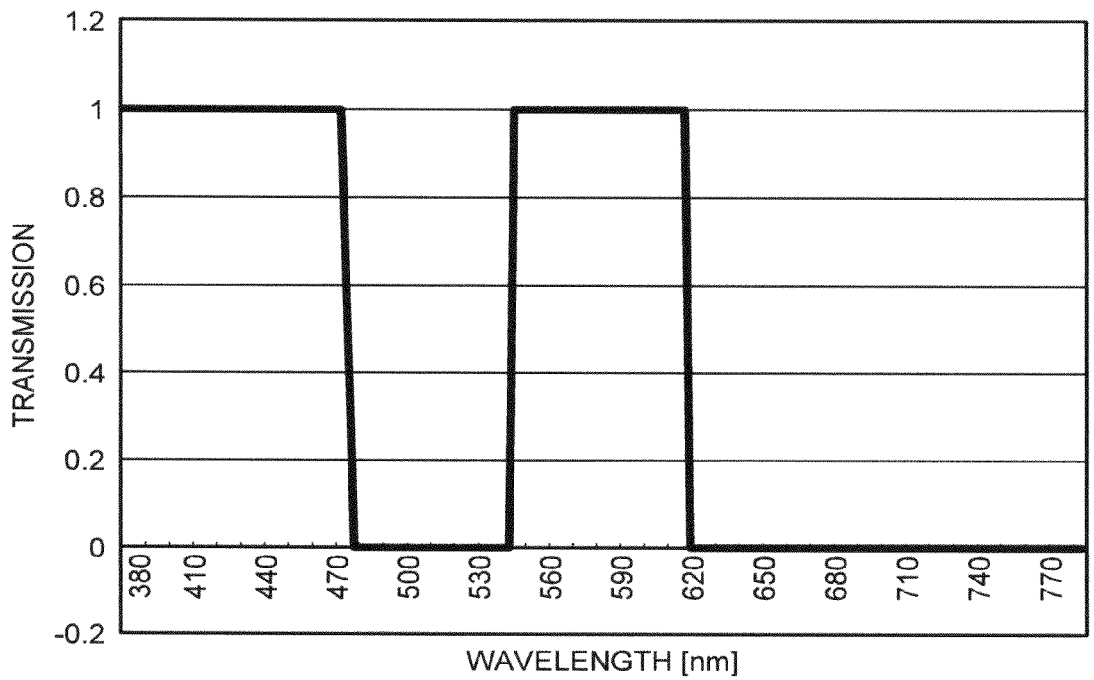
FIG. 6A is a view showing spectral transmittance characteristics of a first optical filter.
Figure 6B:
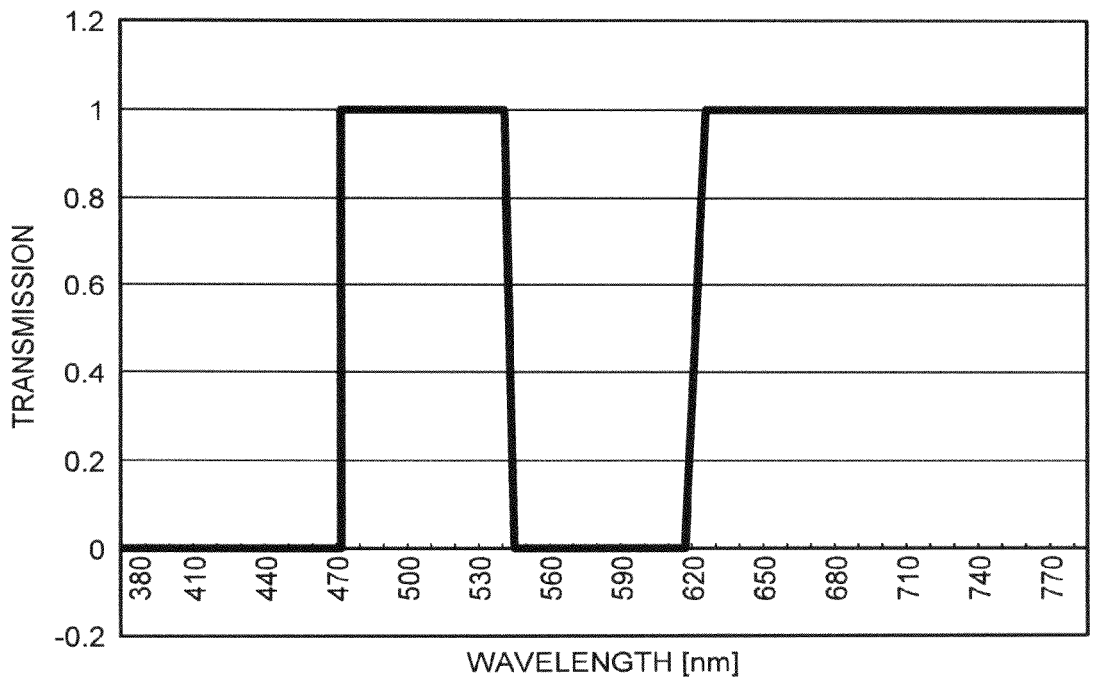
FIG. 6B is a view showing spectral transmittance characteristics of a second optical filter.

The optical filter 1013 is composed of a first optical filter 1013a having the spectral transmittance characteristics shown in FIG. 6A and a second optical filter 1013b having the spectral transmittance characteristics shown in FIG. 6B, and for example, first imaging is performed first using the first optical filter 1013a, and after that, this is switched to the second optical filter 1013b by the optical filter switching unit 1014 and second imaging is performed. A 3-band image is obtained in each of the first and second imagings, and the 6-band multiband image is obtained by combining both results. The imaged multiband image is stored in the storage unit 112.

Next, the first spectrum estimating unit 102 reads image information regarding the 6-band multiband image imaged by the multiband image imaging unit 101 from the storage unit 112 to estimate first spectral transmittance (spectrum of the object) based on the read image information (step S2). The process thereafter is performed according to the procedure similar to that disclosed in the above-mentioned non-patent document, and a Wiener estimation is used as in the non-patent document as an estimation method at step S2. Specifically, an equation (3)

$$\hat{T}(x,y) = R_{SS}(FSE)^t((FSE)R_{SS}(FSE)^t + R_{NN})^{-1} G(x,y) \quad (3),$$

which is described also in the section of the background art, is used to convert a matrix representation $G(x,y)$ of a pixel value at a point (x, y) on the multiband image, thereby estimating the matrix representation $\hat{T}(x, y)$ of the spectral transmittance at a corresponding point on the specimen. Here, $\hat{T}(x, y)$ represents an estimation value of the first spectral transmittance. Hereinafter, the estimation value of the spectral transmittance is simply referred to as "spectral transmittance". Meanwhile, meaning of each symbol in the equation (3) is as described in the section of the background of art.

Here, spectral transmittance F of the optical filter 1013, spectral sensitivity characteristics S of the RGB camera 1015, and spectral radiance characteristics E of the illuminating unit 1011 are measured in advance with a spectrometer after selecting a device to be used. Meanwhile, although the spectral transmittance of the optical system 1012 approximates 1.0 herein, when deviation from the an approximation value 1.0 is not acceptable, the spectral transmittance of the optical system 1012 may also be measured in advance and multiplied by the spectral radiance characteristics E of the illumination.

An autocorrelation matrix $R_{SS}$ of the spectral transmittance of the specimen is obtained by preparing a typical H&E stained pathological specimen and measuring the spectral transmittance of a plurality of points with the spectrometer. At that time, it is better to measure approximately 100 points in the specimen without bias, in order to improve statistical accuracy. On the other hand, an autocorrelation matrix $R_{NN}$ of noise of the camera is obtained by performing the first and second imagings with the multiband image imaging unit 101 in a state in which the specimen is not placed to obtain variance of the pixel value for each band of the obtained 6-band image, and generating the matrix having the same as a diagonal component. However, it is supposed that there is no noise correlation between bands. The first spectral transmittance $\hat{T}(x, y)$ obtained in this manner is stored in the storage unit 112.

Consequently, the dye amount estimating unit 103 reads the first spectral transmittance $\hat{T}(x, y)$ estimated by the first spectrum estimating unit 102 from the storage unit 112, and converts the read first spectral transmittance $\hat{T}(x, y)$ to estimate the dye amount (step S3). The dyes to be processed here are hematoxylin, eosin which stains the cytoplasm, and eosin which stains the red blood cell, as in the non-patent document, and they are abbreviated as dyes H, E, and R, respectively. In the specific process, the following equation (7)

$$-\log \hat{t}(x,y,\lambda) = k_H(\lambda) \cdot d_H + k_E(\lambda) \cdot d_E + k_R(\lambda) \cdot d_R \quad (7),$$

derived from a Lambert-Beer law is made simultaneous with a plurality of wavelengths $\lambda$, and this is solved for $d_H$, $d_E$ and $d_R$. The meaning of each symbol in the equation (7) is as described above, and especially, $\hat{t}(x, y, \lambda)$ is a component corresponding to the wavelength $\lambda$ of the matrix $\hat{T}(x, y, \lambda)$.

As one example, considering a case in which the equation (7) is made simultaneous with three wavelengths $\lambda_1$, $\lambda_2$ and $\lambda_3$, the matrix representation as in the following equation (9) is obtained.

$$\begin{pmatrix} -\log \hat{t}(x, y, \lambda_1) \\ -\log \hat{t}(x, y, \lambda_2) \\ -\log \hat{t}(x, y, \lambda_3) \end{pmatrix} = \begin{pmatrix} k_H(\lambda_1) & k_E(\lambda_1) & k_R(\lambda_1) \\ k_H(\lambda_2) & k_E(\lambda_2) & k_R(\lambda_2) \\ k_H(\lambda_3) & k_E(\lambda_3) & k_R(\lambda_3) \end{pmatrix} \begin{pmatrix} d_H \\ d_E \\ d_R \end{pmatrix} \quad (9)$$

Therefore, $d_H$, $d_E$ and $d_R$ are calculated as in the following equation (10).

$$\begin{pmatrix} d_H \\ d_E \\ d_R \end{pmatrix} = \begin{pmatrix} k_H(\lambda_1) & k_E(\lambda_1) & k_R(\lambda_1) \\ k_H(\lambda_2) & k_E(\lambda_2) & k_R(\lambda_2) \\ k_H(\lambda_3) & k_E(\lambda_3) & k_R(\lambda_3) \end{pmatrix}^{-1} \begin{pmatrix} -\log \hat{t}(x, y, \lambda_1) \\ -\log \hat{t}(x, y, \lambda_2) \\ -\log \hat{t}(x, y, \lambda_3) \end{pmatrix} \quad (10)$$

The dye amounts $d_H$, $d_E$ and $d_R$ estimated in this manner are stored in the storage unit 112.

After that, the second spectrum estimating unit 104 reads the dye amount estimated by the dye amount estimating unit 103 from the storage unit 112, and converts the read dye amount to synthesize second spectral transmittance (first spectrum) (step S4). At step S4, a term for the dye R is eliminated from the equation (8), and the following equation (11) obtained by setting coefficients $\alpha_H$ and $\alpha_E$ to 1 is used.

$$t^{**}(x,y,\lambda) = \exp(-(k_H(\lambda) \cdot d_H + k_E(\lambda) \cdot d_E)) \quad (11)$$

Here, $t^{}(x, y, \lambda)$ is a component corresponding to the wavelength $\lambda$ out of the second spectral transmittance. When $t^{}(x, y, \lambda)$ for a plurality of wavelengths $\lambda$ obtained by using the equation (11) is summarized into a matrix form and is expressed as $T^{}(x, y, \lambda)$, this $T^{}(x, y, \lambda)$ represents the second spectral transmittance. The second spectral transmittance $T^{**}(x, y, \lambda)$ obtained in this manner is stored in the storage unit 112.

Next, the spectral subtractor 105 reads the first and second spectral transmittances $\hat{T}(x, y)$ and $T^{*}(x, y)$ from the storage unit 112, and calculates a difference spectrum by subtracting the second spectral transmittance $T^{*}(x, y)$ from the first spectral transmittance $\hat{T}(x, y)$, $$T_{diff}(x,y) = \hat{T}(x,y) - T^{**}(x,y) \quad (12)$$

(step S5). The difference spectrum $T_{diff}(x, y)$ obtained by the equation (12) is stored in the storage unit 112.

Here, a reason for obtaining the difference spectrum $T_{diff}(x, y)$ is as follows. Although the dye amount estimating unit 103 converts the first spectral transmittance $\hat{T}(x, y)$ estimated by the first spectrum estimating unit 102 to the dye amount, physical model used at that time is the Lambert-Beer law only. The Lambert-Beer law is obtained by formulating attenuation of light passing through a translucent substance assuming that there is no refraction and scattering, but the refraction and the scattering might occur in the actual stained specimen. Therefore, when modeling the attenuation of light by the stained specimen only by the Lambert-Beer law, error that accompanies the modeling occurs, so that even when the spectral transmittance of the stained specimen is calculated by applying the dye amount estimated from the first spectral transmittance $\hat{T}(x, y)$ to the Lambert-Beer law again, this does not conform to the first spectral transmittance $\hat{T}(x, y)$ in general. However, model construction including the refraction and the scattering in a living specimen is extremely difficult, and this is practically impracticable. Then, in this embodiment, it is configured to bring out the error of modeling including the effect of the refraction and the scattering as the difference spectrum, and combine the same with the information capable of modeling, thereby improving general accuracy.

In this embodiment, when calculating the second spectral transmittance $T^{}(x, y)$, the term for the dye R (eosin, which stains the red blood cell) is eliminated (refer to the equation (11)). Therefore, the second spectral transmittance $T^{}(x, y)$ does not include the attenuation due to the dye R. Instead, the attenuation of light caused by the dye R included in the first spectral transmittance $\hat{T}(x, y)$ is given to a following process in a state included in the difference spectrum $T_{diff}(x, y)$.

Continuously, the dye amount correcting unit 106 performs correction of multiplying coefficients (first coefficients) $\alpha_H$ and $\alpha_E$ by the dye amounts $d_H$ and $d_E$, respectively (step S6). The dye amounts after the correction are $\alpha_H d_H$ and $\alpha_E d_E$, respectively. Although the initial values of the coefficients $\alpha_H$ and $\alpha_E$ are 1, the values can be changed by the input from the operating unit 111, as described later. Meanwhile, it is also possible to further introduce the coefficients (second coefficients) $\beta_H$ and $\beta_E$ to correct the dye amounts by the forms $\alpha_H d_H + \beta_H$ and $\alpha_E d_E + \beta_E$. It is possible to add a bias component to the estimated dye amount in this form, so that an emphatic effect different from a case in which the coefficient is multiplied only is obtained. The initial values of the coefficients $\beta_H$ and $\beta_E$ may be set to 0. The dye amounts corrected in this manner are stored in the storage unit 112.

The dye amount $d_R$ of the dye R is eliminated from the correction object at the above-described step S6 because the dye R is not susceptible to the effect by a staining state and generally displays vivid red, so that it is not practically necessary to be corrected. In addition, color saturation of the dye R is higher than those of the dyes H and E, so that the color in a finally output RGB image is prone to unnatural due to the effect of the error which occurs in modeling and calculation process, and this tendency is further emphasized by correcting the dye amount. Therefore, unless there is some positive reason to correct the dye amount $d_R$ of the dye R, this is preferably eliminated from the correction object.

In this embodiment, not only by eliminating the dye R from the correction object, but also by processing the same by including in the difference spectrum $T_{diff}(x, y)$ as described above, the effect of the error in an area including the dye R (that is to say, a red blood cell area) to the finally output RGB image is reduced.

Consequently, the third spectrum estimating unit 107 reads the dye amount corrected by the dye amount correcting unit 106 from the storage unit 112, and converts the read dye amount to synthesize third spectral transmittance (second spectrum) (step S7). At step S7, the following equation (13) is obtained by eliminating the term for the dye R from the equation (8) shown in the section of the background art.

$$t^{***}(x,y,\lambda) = \exp(-(k_H(\lambda) \cdot \alpha_H d_H + k_E(\lambda) \cdot \alpha_E d_E)) \quad (13)$$

Here, $t^{*}(x, y, \lambda)$ is a component corresponding to the wavelength k out of the third spectral transmittance. When $t^{*}(x, y, \lambda)$ for a plurality of wavelengths obtained by using the equation (13) is summarized into the matrix form and is expressed as $T^{*}(x, y, \lambda)$, this $T^{*}(x, y, \lambda)$ represents the third spectral transmittance. Third spectral transmittance data obtained in this manner is stored in the storage unit 112.

After that, the spectrum adder 108 reads the third spectral transmittance $T^{***}(x, y, \lambda)$ obtained by the third spectrum estimating unit 107 and the difference spectrum $T_{diff}(x,y,\lambda)$ obtained by the spectrum subtractor 105 from the storage unit 112 to add, and synthesizes fourth spectral transmittance (third spectrum) (step S8).

$$\tilde{T}(x,y) = T^{***}(x,y) + T_{diff}(x,y) \quad (14)$$

The fourth spectral transmittance $\tilde{T}(x,y)$ synthesized in this manner is stored in the storage unit 112. Hereinafter, $\tilde{T}$ is sometimes represented as T.

As described above, the difference spectrum $T_{diff}(x, y)$ includes modeling error due to the effect of the scattering and diffusion and the attenuation of light by the dye R (eosin, which stains the red blood cell). By adding the same to the attenuation of light by the dyes H and E modeled by the Lambert-Beer law, it is possible to calculate the spectral transmittance data having high accuracy with reduced effect of the modeling error.

Next, the image synthesizer 109 reads the fourth spectral transmittance T(x, y) from the storage unit 112 and synthesizes the RGB image, which is a display image, using the read fourth spectral transmittance T(x, y) (step 9). Specifically, when converting T(x, y) to an RGB value $G_{RGB}(x, y)$, the following equation (15) obtained by eliminating a noise component N in the equation (2) is used.

$$G_{RGB}(x,y)=FSE\hat{T}(x,y) \quad (15)$$

Here, a matrix S corresponds to the spectral sensitivity characteristics of the RGB camera 1015. It is simple to use the spectral sensitivity characteristics of the RGB camera 1015 that images the multiband image, but this may be those of another RGB camera. At step S9, the RGB image having the same width and height as the imaged multiband image is obtained by repeatedly performing the process to convert the fourth spectral transmittance T(x, y) to the RGB value for all of the points (x, y). The RGB image synthesized in this manner is stored in the storage unit 112.

Figure 7:
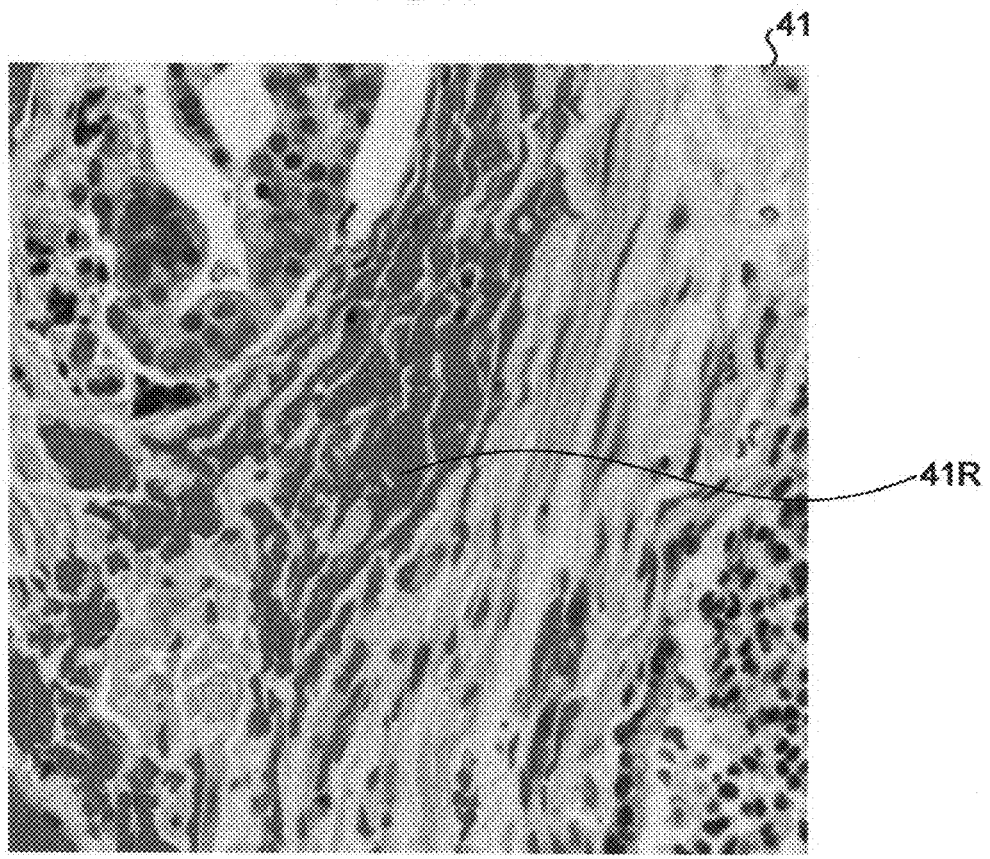
FIG. 7 is a view showing a display example of an RGB image in a display unit.
Figure 10:
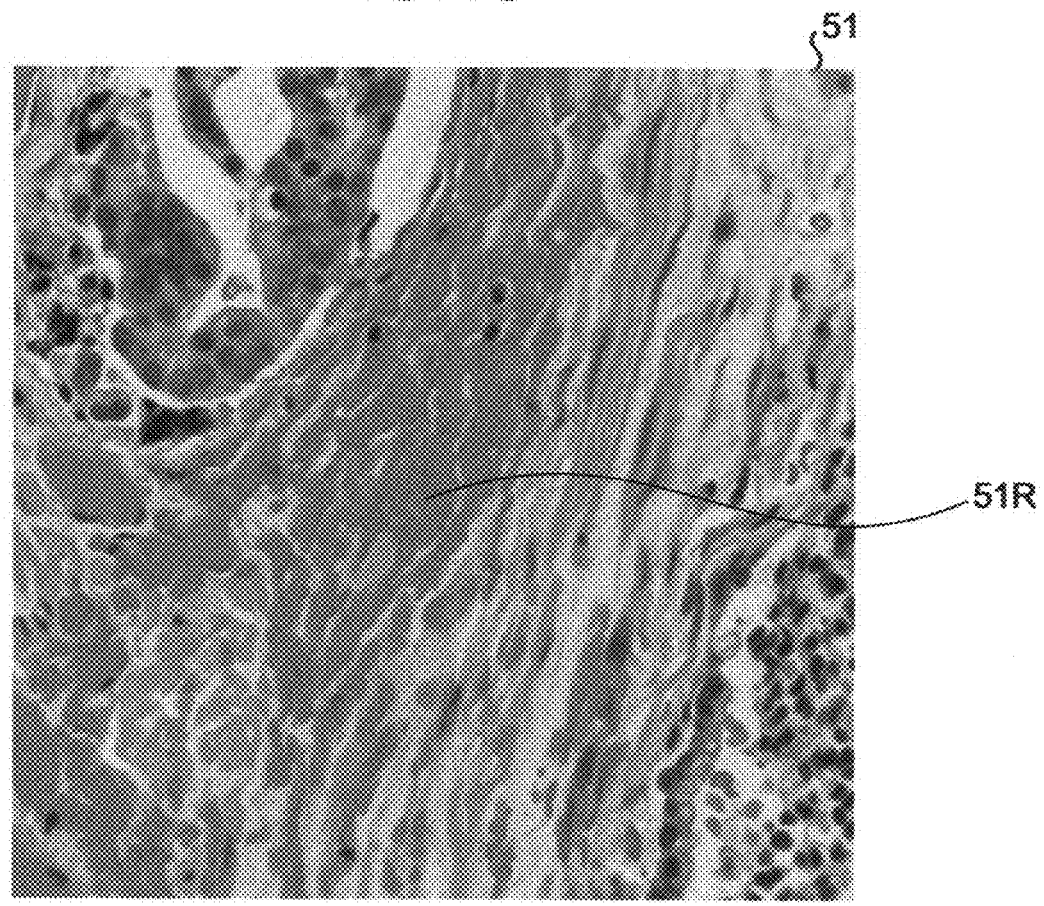
FIG. 10 is view showing a display example of the RGB image according to a conventional method.

The display unit 110 displays the RGB image generated by the image synthesizer 109 and stored in the storage unit 112. FIG. 7 is a view showing a displaying example of the RGB image in the display unit 110. An RGB image 41 shown in the drawing is obtained by executing the image processing method according to this embodiment to the image obtained by imaging the same portion as the RGB image 51 in FIG. 10 described in the section of the background art. When comparing the RGB image 41 with the RGB image 51, a red blood cell area 41R of the RGB image 41 is more tinged with red than a red blood cell area 51R of the RGB image 51, and displays more natural color without causing the unnatural color variation in the image. Also, the RGB image 41 totally displays the natural color for other areas.

Meanwhile, as the display unit 110, a general flat panel display (such as a liquid crystal and an organic EL) or a CRT display may be used. When a plurality of RGB images are stored in the storage unit 112, a mechanism with which the user can select the RGB image to be displayed may be added.

Figure 8A:
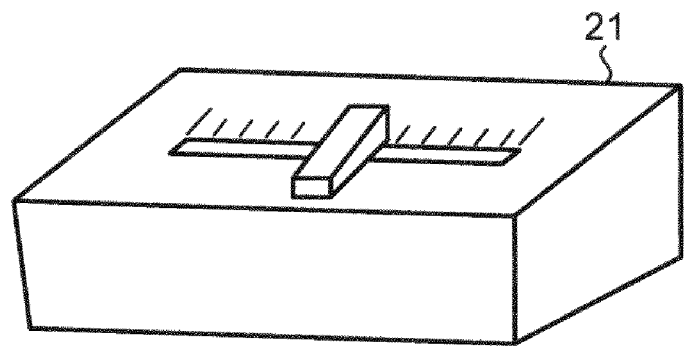
FIG. 8A is a view showing a configuration example (first example) of an operating unit.
Figure 8B:
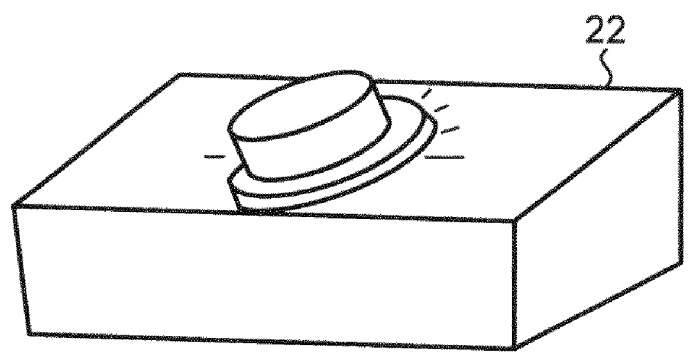
FIG. 8B is a view showing the configuration example (second example) of the operating unit.
Figure 8C:
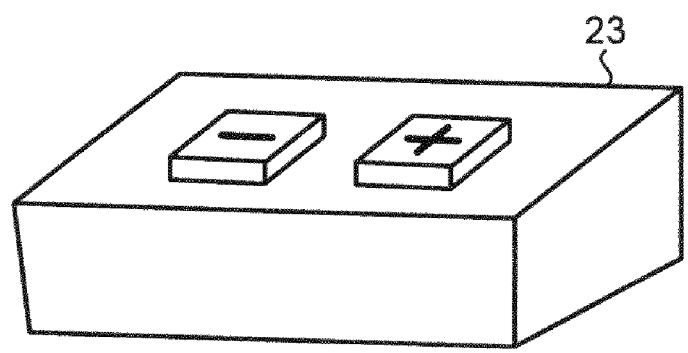
FIG. 8C is a view showing the configuration example (third example) of the operating unit.
Figure 9A:
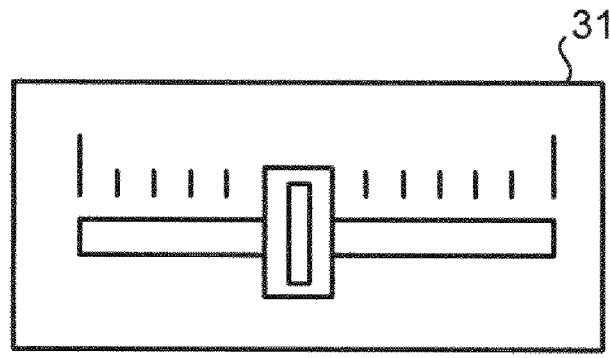
FIG. 9A is a view showing a configuration example (first example) of a graphical user interface.
Figure 9B:
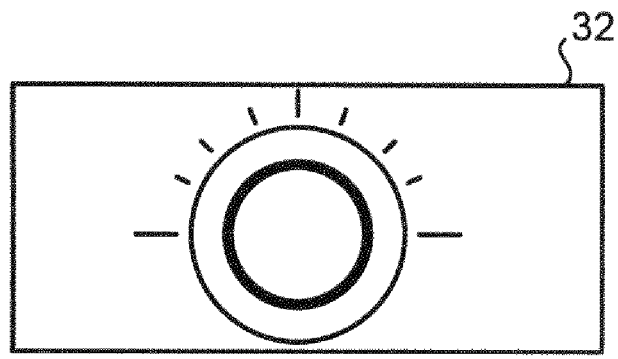
FIG. 9B is a view showing the configuration example (second example) of the graphical user interface.
Figure 9C:
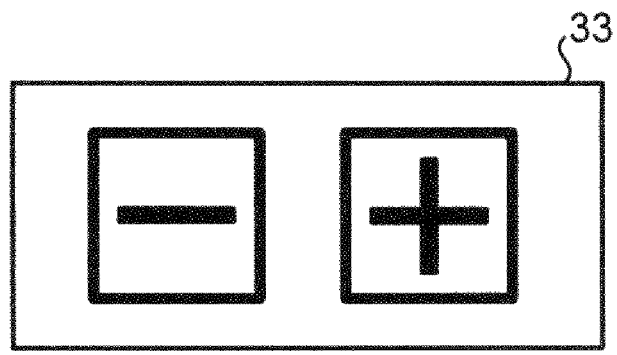
FIG. 9C is a view showing the configuration example (third example) of the graphical user interface.

In the above-described image processing method, it is also possible to provide a dye amount correction function adjustable by the user himself. In this case, the user inputs a correction instruction signal to instruct the correction of the dye amount by operating the operating unit 111 while observing the RGB image displayed on the display unit 110. The correction instruction signal includes, for example, an instruction to change the coefficients $\alpha_H$ and $\alpha_E$ used in the dye amount correcting unit 106. The operating unit 111 may be realized by devices such as a slider 21 (FIG. 8A), a dial 22 (FIG. 8B), and a push button 23 (FIG. 8C). A configuration in which any of graphical user interfaces 31 (FIG. 9A), 32 (FIG. 9B) and 33 (FIG. 9C), which imitatively display the devices on a screen, is displayed on the screen of the display unit 110 and is operated by a mouse and a touch panel is also possible. By providing such an operating unit 111, the user may simply input the correction instruction signal including change of the coefficients $\alpha_H$ and $\alpha_E$.

Meanwhile, although the devices and the graphical user interfaces for correcting one dye are shown in FIGS. 8A to 8C and 9A to 9C, it is also possible to simultaneously input the correction instruction signal of one or a plurality of the dyes by a plurality of them or a combination of them.

In response to the correction instruction signal input from the operating unit 111 in this manner, the coefficients $\alpha_H$ and $\alpha_E$ used in the dye amount correcting unit 106 are immediately changed, and a correction process of the dye amount (step S6) is executed again in the dye amount correcting unit 106. Next to the dye amount correcting process, the third spectrum estimating unit 107, the spectrum adder 108, and the image synthesizer 109 perform the above-described processes (steps S7 to S9), respectively, and the RGB image synthesized again is displayed on the display unit 110 (step S10).

When providing the here described correction function of the dye amount by the user himself to the image processing apparatus 1, it is possible to immediately reflect a result of the correction operation of the dye amount as the RGB image by mounting a high-speed processor on the image processing apparatus 1, so that the user can correct the dye amount by confirming the operation contents, thereby significantly improving the operability thereof.

According to one embodiment of the present invention described above, it is possible to correct the staining variation by using the image processing including the function to virtually adjusting the staining dye amount without causing the unnatural color variation in the image.

Also, according to this embodiment, by processing the modeling error caused by the refraction and the scattering when applying the Lambert-Beer law to the living specimen as the difference spectrum, it becomes possible to perform a spectral data process having high accuracy, which is not susceptible to the effect of the modeling error. As a result, the RGB image more preferable in performing the visual presentation can be obtained.

Meanwhile, in this embodiment, although the dye R is eliminated from the object of the dye amount correction in the second spectrum estimating unit 104, the dye amount correcting unit 106, and the third spectrum estimating unit 107, when it is desired to especially add them to the correction object, following equations (11)' and (13)' may be used in place of the equations (11) and (13), respectively.

$$t^{**}(x,y,\lambda)=\exp(-(k_H(\lambda)\cdot d_H+k_E(\lambda)\cdot d_E+k_R(\lambda)\cdot d_R)) \quad (11)'$$

$$t^{***}(x,y,\lambda)=\exp(-(k_H(\lambda)\cdot \alpha_H d_H+k_E(\lambda)\cdot \alpha_E d_E+k_R(\lambda)\cdot \alpha_R d_R)) \quad (13)'$$

In this case, the dye amount $d_R$ of the dye R is corrected in the form of $\alpha_R d_R$ or $\alpha_R d_R+\beta_R$ using the first and second coefficients $\alpha_R$ and $\beta_R$. Although the initial values of the coefficients $\alpha_R$ and $\beta_R$ are 1 and 0, respectively, the values may be made changeable by the input from the operating unit 111.

Also, although the second spectrum estimating unit 104 and the third spectrum estimating unit 107 are separated in this embodiment, if the coefficients $\alpha_H$ and $\alpha_E$ are set to 1 in the third spectrum estimating unit 107, the process becomes identical to that of the second spectrum estimating unit 104. Therefore, the configuration that the second and third spectrum estimating units 104 and 107 are integrated and are separately used by switching the coefficients may also be used. Thus configured, the device configuration is simplified and a lower cost may be realized.

The CPU provided in the image processing apparatus 1 executes the calculation process regarding the image processing method by reading the image processing program for executing the image processing method according to this embodiment from the storage unit 112. Meanwhile, the image processing program according to this embodiment may be recorded in a computer-readable recording media such as a flexible disk, a CD-ROM, a DVD-ROM, and a flash memory and is widely distributed. In this sense, the image processing apparatus 1 may be provided with an auxiliary storage device capable of reading any of the above-described various recording media.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for performing an image processing on an image, comprising;
   a storage unit for storing image information regarding the image;
   a first spectrum estimating unit for reading the image information from the storage unit and estimating a spectrum of an object based on the read image information;
   a dye amount estimating unit for estimating a plurality of dye amounts included in the object using the spectrum of the object estimated by the first spectrum estimating unit;
   a second spectrum estimating unit for synthesizing a first spectrum using the plurality of dye amounts estimated by the dye amount estimating unit;
   a spectrum subtractor for calculating a difference spectrum by subtracting the first spectrum synthesized by the second spectrum estimating unit from the spectrum of the object;
   a dye amount correcting unit for correcting at least a part of the plurality of dye amounts estimated by the dye amount estimating unit;
   a third spectrum estimating unit for synthesizing a second spectrum using the dye amount corrected by the dye amount correcting unit;
   a spectrum adder for synthesizing a third spectrum by adding the second spectrum synthesized by the third spectrum estimating unit and the difference spectrum; and
   an image synthesizer for synthesizing a display image from the third spectrum synthesized by the spectrum adder.

2. The image processing apparatus according to claim 1, wherein the display image is an RGB image.

3. The image processing apparatus according to claim 1, wherein the number of dye amounts estimated from the spectrum of the object is larger than the number of dye amounts used for synthesizing the first spectrum.

4. The image processing apparatus according to claim 1, wherein the number of dye amounts estimated from the spectrum of the object is equal to the number of dye amounts used for synthesizing the first spectrum.

5. The image processing apparatus according to claim 1, wherein the number of dye amounts used for synthesizing the first spectrum and the number of dye amounts used for synthesizing the second spectrum are equal to each other.

6. The image processing apparatus according to claim 1, further comprising a display unit for displaying the display image.

7. The image processing apparatus according to claim 1, further comprising an operating unit to which a correction instruction signal for instructing correction of the dye amount is input.

8. The image processing apparatus according to claim 7, wherein information regarding a coefficient used when correcting the dye amount is included in the correction instruction signal.

9. The image processing apparatus according to claim 7, wherein the operating unit includes any one of a slider, a dial, and a push button.

10. The image processing apparatus according to claim 7, wherein the operating unit includes a graphical user interface, which imitates any one of a slider, a dial, and a push button.

11. The image processing apparatus according to claim 10, wherein the graphical user interface is displayed in a same screen as the display image.

12. The image processing apparatus according to claim 1, wherein the dye amount correcting unit corrects the dye amount by multiplying a first coefficient by the dye amount.

13. The image processing apparatus according to claim 1, wherein the dye amount correcting unit corrects the dye amount by adding a second coefficient to the dye amount.

14. The image processing apparatus according to claim 7, wherein the dye amount correcting unit, the third spectrum estimating unit, the spectrum adder, and the image synthesizer perform a process based on contents of the correction instruction signal input by the operating unit, and
   the display unit displays the display image to which the process based on the contents of the correction instruction signal is reflected.

15. The image processing apparatus according to claim 1, wherein the object is a stained living specimen.

16. The image processing apparatus according to claim 15, wherein the object is a pathological specimen.

17. The image processing apparatus according to claim 16, wherein the dye amount estimated by the dye amount estimating unit includes hematoxylin and eosin.

18. The image processing apparatus according to claim 17, wherein the dye amount estimated by the dye amount estimating unit further includes eosin which stains a red blood cell.

19. The image processing apparatus according to claim 1, wherein the first spectrum estimating unit uses a Wiener estimation when estimating the spectrum of the object.

20. The image processing apparatus according to claim 1, wherein the first spectrum estimating unit uses a Lambert-Beer law when estimating a plurality of dye amounts included in the object.

21. An image processing method for performing an image processing on an image, the image processing method comprising:
   reading the image information from a storage unit;
   estimating a spectrum of an object based on the read image information;
   estimating a plurality of dye amounts included in the object using the estimated spectrum of the object;
   synthesizing a first spectrum using the estimated dye amounts;
   calculating a difference spectrum by subtracting the first spectrum from the spectrum of the object;
   correcting at least a part of the estimated dye amounts;
   synthesizing a second spectrum using the corrected dye amount;
   synthesizing a third spectrum by adding the second spectrum; and
   synthesizing a display image from the third spectrum.

22. A computer program product having a computer readable medium including programmed instructions performing an image processing on an image, wherein the instructions, when executed by a computer, cause the computer to perform:
   reading the image information from a storage unit;
   estimating a spectrum of an object based on the read image information;
   estimating a plurality of dye amounts included in the object using the estimated spectrum of the object;
   synthesizing a first spectrum using the estimated dye amounts;

calculating a difference spectrum by subtracting the first spectrum from the spectrum of the object;
correcting at least a part of the estimated dye amounts;
synthesizing a second spectrum using the corrected dye amount;
synthesizing a third spectrum by adding the second spectrum; and
synthesizing a display image from the third spectrum.

* * * * *